(12) United States Patent
Ryu

(10) Patent No.: US 9,271,473 B2
(45) Date of Patent: Mar. 1, 2016

(54) SEPARABLE TOILET PAD FOR HOUSEBREAKING ANIMAL COMPANIONS

(76) Inventor: Jong Hyun Ryu, Yongin-si (KR)

(*) Notice: Subject to any disclaimer, the term of this patent is extended or adjusted under 35 U.S.C. 154(b) by 166 days.

(21) Appl. No.: 13/992,245

(22) PCT Filed: Dec. 20, 2011

(86) PCT No.: PCT/KR2011/009840
§ 371 (c)(1),
(2), (4) Date: Jun. 7, 2013

(87) PCT Pub. No.: WO2012/086996
PCT Pub. Date: Jun. 28, 2012

(65) Prior Publication Data
US 2013/0269624 A1    Oct. 17, 2013

(30) Foreign Application Priority Data

Dec. 22, 2010 (KR) .......... 10-2010-0132820
May 6, 2011 (KR) .......... 10-2011-0042892
Sep. 17, 2011 (KR) .......... 10-2011-0093764

(51) Int. Cl.
 A01K 29/00   (2006.01)
 A01K 1/01    (2006.01)
 A01K 1/015   (2006.01)
 A61F 13/36   (2006.01)
 A61F 15/00   (2006.01)

(52) U.S. Cl.
 CPC ............ *A01K 1/0107* (2013.01); *A01K 1/0152* (2013.01); *A61F 13/36* (2013.01); *A61F 15/00* (2013.01)

(58) Field of Classification Search
 CPC .. A01K 1/0157; A01K 1/0152; A01K 1/0107
 USPC ......... 119/166, 167, 168, 169, 905, 171, 172, 119/173
 See application file for complete search history.

(56) References Cited

U.S. PATENT DOCUMENTS 2,621,139 A * 12/1952 Messing .................. 428/158
4,457,964 A *  7/1984 Kaminstein ................ 428/43
4,781,710 A * 11/1988 Megison et al. ............ 604/378
4,797,310 A *  1/1989 Barby et al. ................ 428/71
5,092,008 A *  3/1992 Okubo ........................ 5/484

(Continued)

FOREIGN PATENT DOCUMENTS

JP   03-113635 U   11/1991
JP   08-019344 A    1/1996

(Continued)

*Primary Examiner* — Kristen C Hayes
*Assistant Examiner* — Ebony Evan
(74) *Attorney, Agent, or Firm* — Revolution IP, PLLC

(57) ABSTRACT

There is disclosed a separable toilet pad for housebreaking animal companions including a protection layer covering an exterior surface; an absorbent layer absorbing and storing urine; and a waterproof layer preventing the absorbed urine from leaking, wherein the waterproof layer includes a waterproof layer cut unit configured to divide or cut the waterproof layer into a plurality of areas, when an external force is applied, and the absorbent layer is arranged in a surface of the waterproof layer and includes a gap with both sides with respect to the waterproof layer cut unit and includes a gap having a distance from both sides of the waterproof cut unit, and a filling part is arranged in the gap and includes a filling part cut unit corresponding to the waterproof layer.

7 Claims, 7 Drawing Sheets

100

B

(56) References Cited

U.S. PATENT DOCUMENTS

| | | | |
|---|---|---|---|
| 5,252,374 A * | 10/1993 | Larsonneur | 428/77 |
| 5,579,722 A * | 12/1996 | Yamamoto et al. | 119/169 |
| 5,712,012 A * | 1/1998 | Forman et al. | 428/43 |
| 6,174,581 B1 * | 1/2001 | Barker | 428/43 |
| 6,177,164 B1 * | 1/2001 | Sullens et al. | 428/40.1 |
| 6,783,831 B2 * | 8/2004 | Cho | 428/43 |
| 8,042,490 B2 * | 10/2011 | Takahashi et al. | 119/171 |
| 8,142,410 B2 * | 3/2012 | Rovaniemi | 604/385.101 |
| 8,852,717 B2 * | 10/2014 | Davis | 428/138 |
| D718,907 S * | 12/2014 | Calimano et al. | D30/161 |
| 9,023,003 B1 * | 5/2015 | Bracci | 604/356 |
| 2002/0037387 A1 * | 3/2002 | Sweeney et al. | 428/43 |
| 2005/0009425 A1 * | 1/2005 | Foote | 442/57 |
| 2008/0236504 A1 * | 10/2008 | Silverman | 119/169 |
| 2009/0044756 A1 * | 2/2009 | Otsuji et al. | 119/169 |
| 2011/0139082 A1 * | 6/2011 | Blagden | 119/171 |

FOREIGN PATENT DOCUMENTS

| | | |
|---|---|---|
| JP | 2007-020469 A | 2/2007 |
| JP | 2010-136669 A | 6/2010 |

* cited by examiner

SEPARABLE TOILET PAD FOR HOUSEBREAKING ANIMAL COMPANIONS

CROSS REFERENCE TO PRIOR APPLICATIONS

This application is a National Stage Application of PCT International Patent Application No. PCT/KR2011/009840 filed on Dec. 20, 2011, under 35 U.S.C. §371, which claims priority to Korean Patent Application Nos. 10-2010-0132820 filed on Dec. 22, 2010, 10-2011-0042892 filed on May 6, 2011 and 10-2011-0093764 filed on Sep. 17, 2011 which are all hereby incorporated by reference in their entirety.

FIELD

The present invention relates to a separable toilet pad for housebreaking animal companions, more particularly, to a separable toilet pad for housebreaking animal companions of which a part is separated by a user freely to be re-used.

BACKGROUND

Recently, people who keep pets are increasing. When keeping a dog as a popular example of pets, an owner has to take it out or do housebreaking for a pet to urinate or defecate on an absorbent paper or pad such as newspapers. Even when the quantity of the pet's urine large in case of using newspapers or auxiliary absorbent paper, the urine happens to leak down out of the newspapers or absorbent paper and then an odor or sanitariness issue might still occur disadvantageously.

To solve such a disadvantage, housebreaking pads for pets that include auxiliary an absorbent layer or a waterproof layer are invented and used to make pets do urination or defecation.

In the drawing herewith, FIG. 1 is an exploded perspective diagram illustrating a conventional toilet pad for housebreaking animal companions for a pet and FIG. 2 is a plane view of the conventional housekeeping pad for pets. As shown in the drawings, the conventional toilet pad for housebreaking animal companions 10 includes an absorbent layer 12 arranged under the absorbent layer to prevent urine or defecation from leaking down, with being formed of a pulp or the like and a waterproof layer 13 formed of a waterproof material, and a protection layer 11 arranged on the absorbent layer 12, with being formed of non-woven fabric.

Even when the pet or animal companion urinates on the conventional housekeeping pad 10, the absorbent layer 12 absorbs the urine and the waterproof layer 13 prevents the urine from leaking down. Accordingly, the owner frequently changes the toilet pad for housebreaking animal companions 10 in a predetermined time period, which is wrapped in vinyl or packed in one box separately, such that the companion animal's excrement can be collected conveniently and indoor cleanness can be maintained.

However, dogs or puppies do not collect and make defecation on a specific spot of the toilet pad for housebreaking animal companions. Some dogs will not make defecation again on the urinated or defecated spot. Because of that, the conventional toilet pad for housebreaking animal companions 10 has to be changed into a new one even though it has a large area not stained with urine or defecation and it costs a great deal.

Even at this time, the conventional toilet pad for housebreaking animal companions partially stained with the urine or defecation could be used continuously. If the toilet pad for housebreaking animal companions stained with the urine or defecation is worn on a companion animal, the urine odor can be permeating the air in the house and it looks unpleasant. In case a dog stands on the pad for the next urine or defecation, one or more legs of the dog would be stained with the former urine or defecation disadvantageously.

Meanwhile, an absorbent product 20 applicable to other usage objects for oil, not the conventional toilet pad for housebreaking animal companions, is disclosed. As shown in FIGS. and 4, such a conventional absorbent product 20 includes a plurality of absorbent layers separated from each other that are disposed between a protection layer 30 and a waterproof layer 50, and a cut portion 35 and 55 provided in a gap (A) between the separated absorbent layers, However, the absorbent product 20 includes no absorbent material arranged in the gap (A) between the absorbent layers 40 and the urine might remain partially, failing to be absorbed. Moreover, the absorbent product 20 could be applied to a toilet pad for housebreaking animal companions according to the present invention. In this instance, if a dog or another companion animal makes urine near the gap (A), the gap (A) can be employed as a guide for the urine, in other words, a flow channel only to flow the urine out of the pad or to a neighboring absorbent layer distant from the absorbent layer. Even a small amount of urine might flow to wet the entire toilet pad for housebreaking animal companions or out of the pad disadvantageously.

In addition, some types of conventional toilet pads for housebreaking animal companions can be formed as roll types of toilet pads for housebreaking animal companions that consist of separable sheets and such a roll type of a toilet pad for housebreaking animal companions can be applied to the conventional toilet pad for housebreaking animal companions shown in FIG. 1. Even in this instance, a sheet of a toilet pad for housebreaking animal companions cannot be separated into plural pieces and there is the disadvantage of material waste.

DETAILED DESCRIPTION OF THE INVENTION

Technical Problem

To overcome the disadvantages, an object of embodiments herewith is to provide a separable toilet pad for housebreaking animal companions of which spots not stained with urine or defecation of a housebroken companion animal are re-usable and that can be easily divided into a plurality of re-useable spots for predetermined portions.

Another object of the embodiments herewith is to provide a separable toilet pad for housebreaking animal companions that is able to reduce the urine of the companion animal spreading out thereon so as to expand a usage time of one sheet.

Technical Solution

To achieve these objects and other advantages and in accordance with the purpose of the embodiments, as embodied and broadly described herein, a separable toilet pad for housebreaking animal companions includes a protection layer covering an exterior surface; an absorbent layer absorbing and storing urine; and a waterproof layer preventing the absorbed urine from leaking, wherein the waterproof layer includes a waterproof layer cut unit configured to divide or cut the waterproof layer into a plurality of areas, when an external force is applied, and the absorbent layer is arranged in a surface of the waterproof layer and includes a gap with both sides with respect to the waterproof layer cut unit and includes a gap having a distance from both sides of the waterproof layer cut unit, and a filling part is arranged in the gap and includes a filling part cut unit corresponding to the waterproof layer.

The filling part and the absorbent layer may be integrally formed with each other.

The filling part and the waterproof layer may be integrally formed with each other.

The absorbent layer includes a spreading-prevention layer configured to prevent the urine from spreading from a portion of the absorbent layer to another portion with respect to the absorbent layer cut unit.

The separable toilet pad for housebreaking animal companions may further include an auxiliary waterproof member configured to prevent the urine from leaking along the waterproof layer cut unit.

The absorbent layer may include an absorbent material spaced apart a predetermine distance from the absorbent layer cut unit.

The waterproof layer cut unit may be arranged in a position corresponding to the absorbent layer cut unit, and the waterproof layer cut unit may be formed of a resin composition for the cut unit that has a material different from the material of the waterproof layer.

The waterproof layer cut unit may be formed of a mixture of Low-Density Polyethylene and a blowing agent.

The waterproof layer cut unit may be formed of High-Density Polyethylene to form a grained cut line.

The waterproof layer cut unit may include a plurality of perforated holes arranged continuously, and the waterproof layer may include a material having a predetermined elastic restoring force.

In another aspect of the present invention, a separable toilet pad for housebreaking animal companions includes a protection layer covering an exterior surface; an absorbent layer absorbing and storing urine; and a waterproof layer preventing the absorbed urine from leaking, wherein the waterproof layer includes a waterproof layer cut unit configured to divide or cut the waterproof layer into a plurality of areas, when an external force is applied, and the absorbent layer includes an absorbent layer cut unit corresponding to the waterproof layer cut unit; and a highly absorbent material, and the protection layer includes a protection layer cut unit corresponding to the waterproof layer cut unit, and the absorbent layer is configured to prevent the highly absorbent material from leaking outside, when the absorbent layer is cut along the absorbent layer cut unit.

Advantageous Effects

The separable toilet pad for housebreaking animal companions according to embodiments has following advantageous effects.

First of all, according to the separable toilet pad for housebreaking animal companions, clean areas stained with no urine or defecation of an animal companion such as a dog or a cat may be re-used immediately. Accordingly, the usage time of the pad can be increased and an economical effect can be gained. Also, there is an effect of waste reduction. In addition, a large sized toilet pad for housebreaking animal companions can be changed into a small-sized one easily and the size of the toilet pad for housebreaking animal companions can be adjustable according to the size of the pet.

Furthermore, only the area stained with the urine or the like may be removed immediately according to the toilet pad for housebreaking animal companions and the other clean areas may be left and re-used. Accordingly, there are effects of odor control and visual cleanness.

Still further, according to the separable toilet pad for housebreaking animal companions of the present invention, the filling part provided in a lattice shape can prevent the urine from spreading out and especially the urine can be kept and stored only in a predetermined area. Accordingly, the other areas where the urine is not spreading can remain as large as possible. Even before cutting the stained area, one sheet of the pad can be used for a longer time effectively.

BEST MODE

Embodiments will be described as follows, referring to the accompanying drawings. Reference will now be made in detail to the specific embodiments of the present invention, examples of which are illustrated in the accompanying drawings. Wherever possible, the same reference numbers will be used throughout the drawings to refer to the same or like parts.

Figure 1:
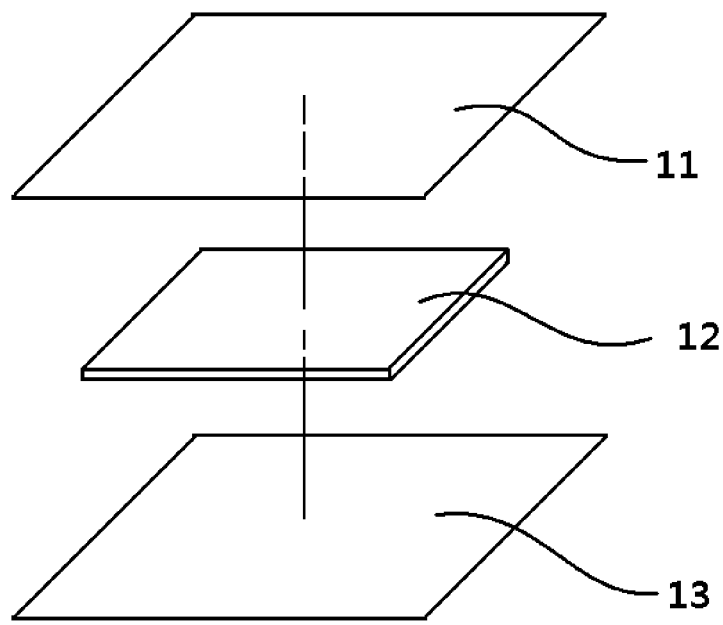
FIG. 1 is an exploded perspective diagram illustrating a conventional toilet pad for housebreaking animal companions.
Figure 2:
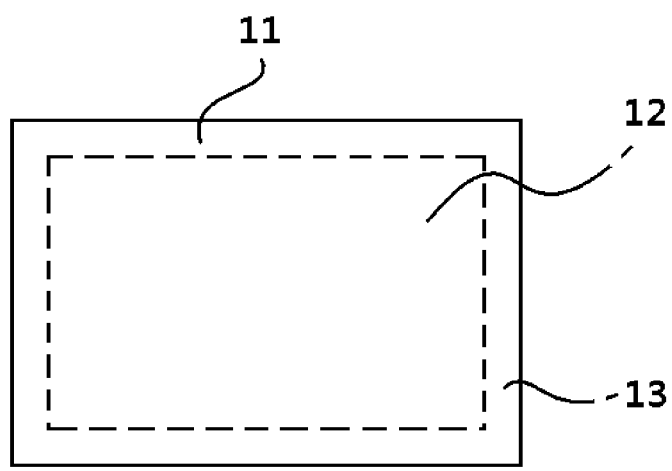
FIG. 2 is a plane diagram of the conventional toilet pad for housebreaking animal companions.
Figure 3:
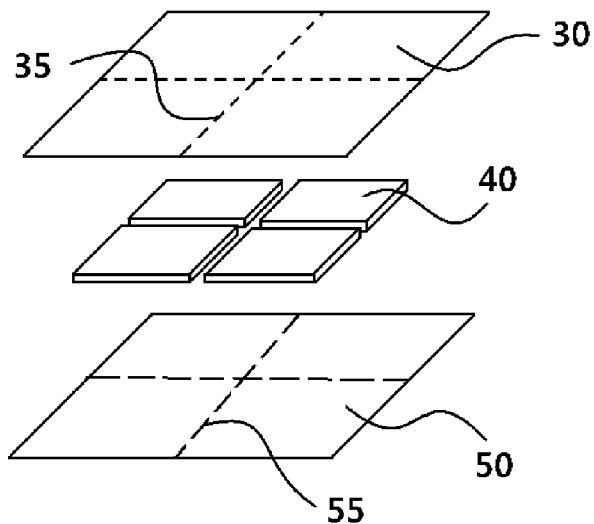
FIG. 3 is an exploded perspective diagram illustrating a conventional absorbent product.
Figure 4:
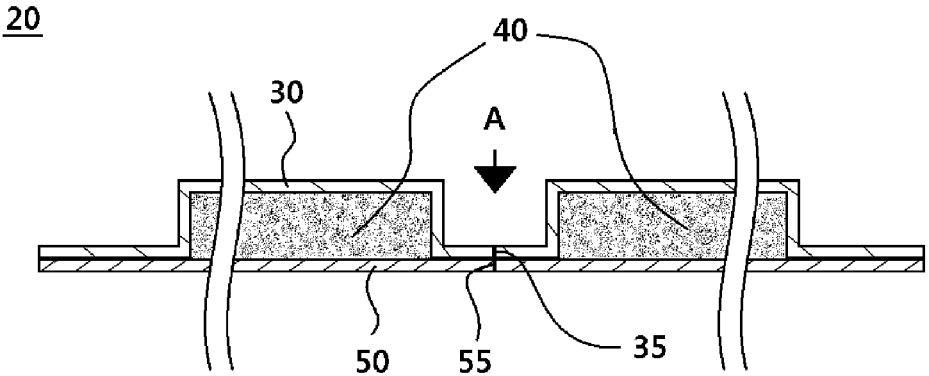
FIG. 4 is a sectional diagram illustrating key parts of the conventional absorbent product shown in FIG. 3.
Figure 5:
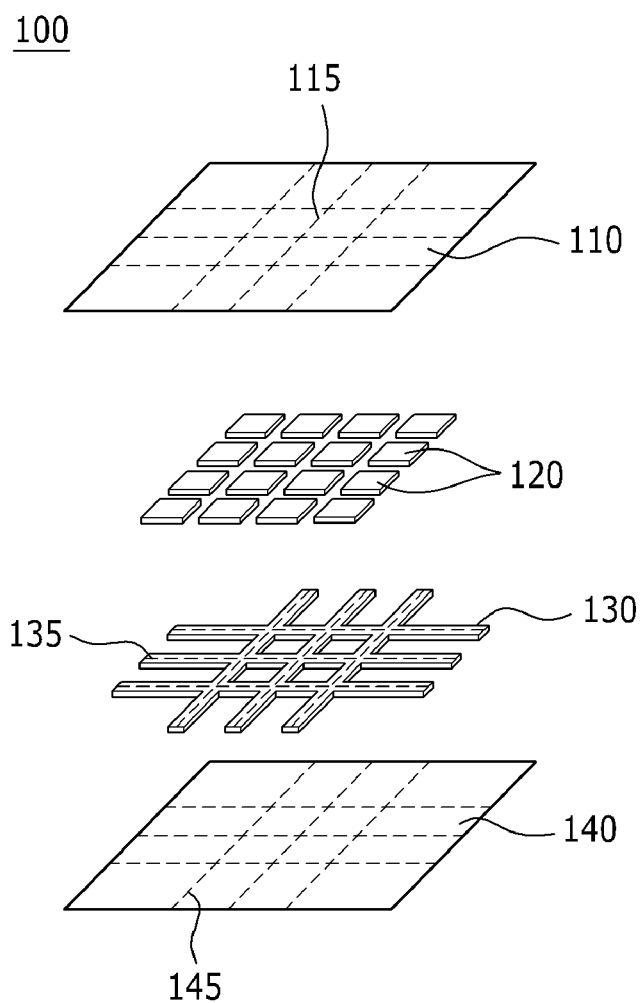
FIG. 5 is an exploded perspective diagram illustrating a separable toilet pad for housebreaking animal companions according to a first embodiment of the present invention.

FIG. 5 is an exploded perspective diagram illustrating a separable toilet pad for housebreaking animal companions according to a first embodiment of the present invention.

A separable toilet pad for housebreaking animal companions 100 according to a first embodiment includes a protection layer 110 that covers an exterior surface thereof, an absorbent layer 120 configured to absorb and store urine, and a waterproof layer 140 configured to prevent the absorbed urine from leaking down. In this instance, the waterproof layer 140 includes a waterproof layer cut unit 145 configured to divide a portion of the waterproof layer 140 into a plurality of areas by using an external force. A plurality of absorbent layers 120 may be arranged in a surface of the waterproof layer 140 and include gaps arranged in both sides with respect to the waterproof layer cut unit 145, being spaced apart from each other. A filling part 130 is filled in the gap and the filling part 130 includes a filling part cut unit 135 coupled to the waterproof layer 140. The protection layer 110 includes a protection layer cut unit 115 corresponding to the waterproof layer cut unit 145.

Although not shown in the drawing in detail, it is preferred that the absorbent layer 120 includes SAP (Super Absorbent Polymers), SAM (Super Absorbent Materials).

A plurality of perforated holes may be arranged along each of the cut units, in other words, the protection layer cut unit 115, the filling part cut unit 135 and the waterproof layer cut unit 145. Alternatively, a connection structure or a thermal connection structure that uses different bonding materials that are separable by the activation of the external force.

Here, the filling part 130 has a predetermined thickness. In case the waterproof layer cut unit 145 configured of perforated holes arranged in a line, urine may be prevented from leaking along the waterproof layer cut unit 145 and SAP and SAM may be prevented from leaking outside after the separable toilet pad for housebreaking animal companions is dividedly cut simultaneously.

A predetermined synthetic resin material or a pulp material may be applied to the filling part 130. When the filling part 130 is formed of such a synthetic material, the filling part 130 may be integrally formed with the waterproof layer 140. When the filling part 130 is formed of a synthetic resin material, specifically, a non-transmissive material, the urine may be prevented from spreading between both neighboring absorbent layers with respect to the filling part cut unit 135 and an overall usage of the separable toilet pad for housebreaking animal companions can be then improved. In this instance, when a dog or another companion animal makes too much urine to be absorbed by a predetermined absorbent layer 120 surrounded by the filling part cut unit 135, the urine might spread a neighboring absorbent layer via the protection layer 110 over the filling unit 130. It can be prevented that too much urine is focused on a predetermined portion of the separable toilet pad for housebreaking animal companions.

A well-known structure in the art can be applied to the structure among the protection layer 110, the absorbent layer 120 and the waterproof layer 140. Various techniques and structure are already released and obvious to those skilled in the art the embodiment pertains to, such that detailed description will be omitted.

Figure 6:
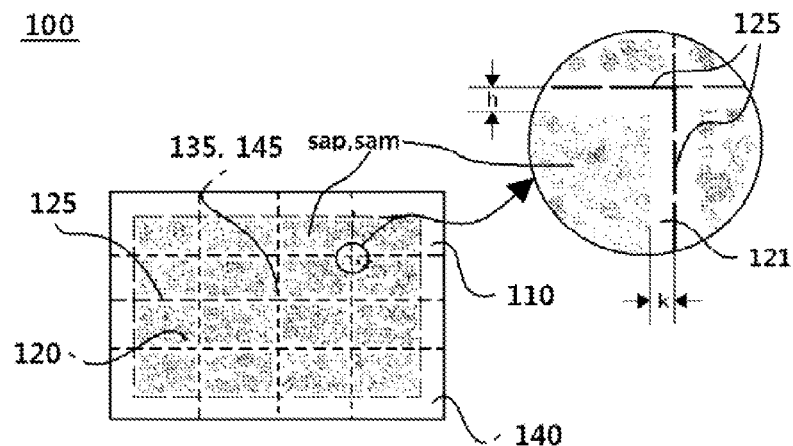
FIG. 6 is a plane diagram illustrating another example of the separable toilet pad for housebreaking animal companions according to the first embodiment.

FIG. 6 is a plane diagram illustrating another example of the separable toilet pad for housebreaking animal companions according to the first embodiment.

As shown in the drawing, the filling part and the absorbent layer 120 are integrally formed with each other in the separable toilet pad for housebreaking animal companions 100 according to another example of the first embodiment.

In other words, according to the first embodiment, the absorbent layer 120 is entirely formed, without the gaps, and a protection layer cut unit 115 and an absorbent layer cut unit 125 is formed in the absorbent layer, corresponding to the waterproof layer cut unit 145.

Meanwhile, in the separable toilet pad for housebreaking animal companions 100 having the filling part 130 and the absorbent layer 120 that are integrally formed with each other according to the example of the first embodiment, SAP and SAM are spaced apart a predetermined distance (h and k) from the absorbent layer cut unit 125 as shown in FIG. 6. Accordingly, the separable toilet pad for housebreaking animal companions 100 can prevent the absorbent materials from coming outside when it is cut into predetermined areas.

Figure 7:
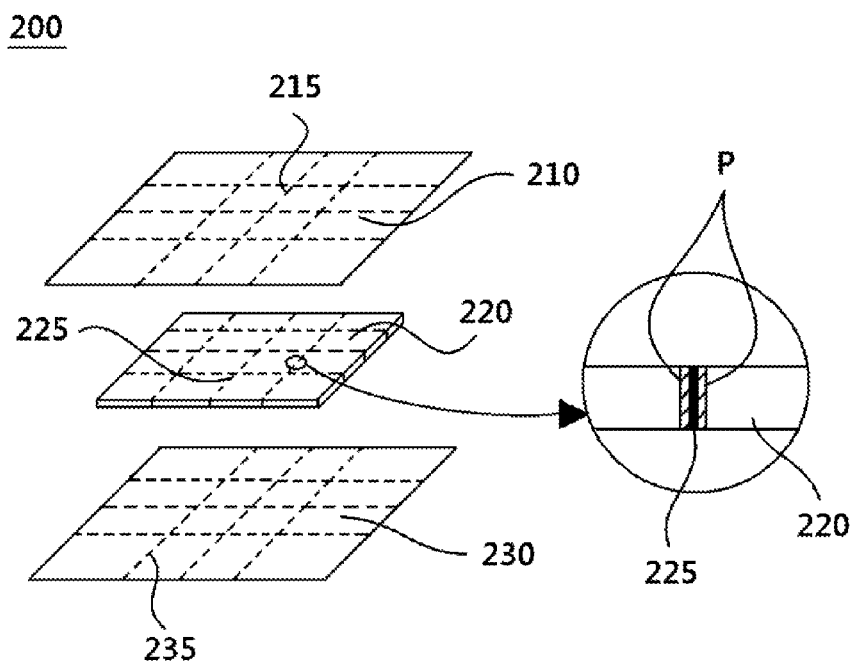
FIG. 7 is an exploded perspective diagram illustrating a separable toilet pad for housebreaking animal companions according to a second embodiment of the present invention.
Figure 8:
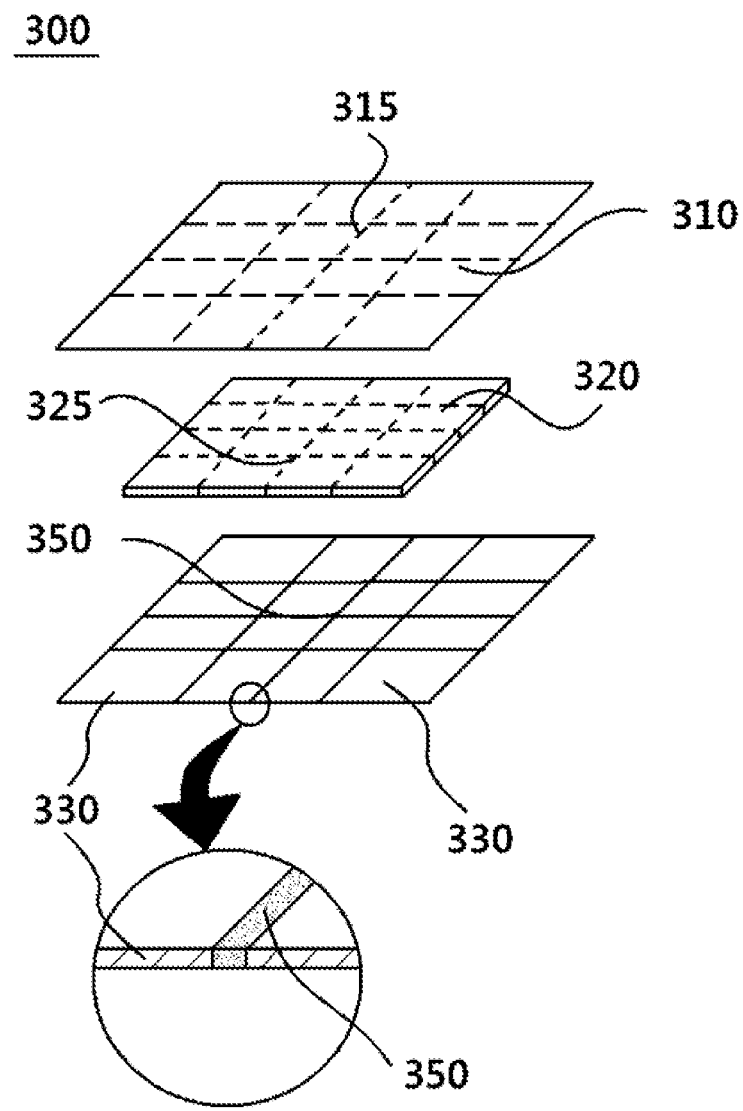
FIG. 8 is an exploded perspective diagram illustrating a separable toilet pad for housebreaking animal companions according to a third embodiment of the present invention.

FIG. 7 is an exploded perspective diagram illustrating a separable toilet pad for housebreaking animal companions according to a second embodiment of the present invention;

As shown in the drawing, a separable toilet pad for housebreaking animal companions 200 according to a second embodiment includes a protection layer 210 having a protection layer cut unit 215, a waterproof layer 230 having a waterproof layer cut unit 235 corresponding to the projection layer cut part 215, and an absorbent layer 220 having a waterproof layer 230 having a waterproof layer cut unit 235 arranged in a position corresponding to the protection layer cut unit 215, and a absorbent layer 220 having an absorbent layer cut unit 225 arranged in a position corresponding to each of the cut units 215 and 235. The absorbent layer 220 is provided between the protection layer 210 and the waterproof layer 230.

As shown in the enlarged view of FIG. 7, a spreading-prevention layer (P) is arranged in each of sides with respect to the absorbent layer cut unit 225 to prevent the urine from spreading between neighboring portions of the absorbent layer cut unit 225. The spreading prevention layer (P) is formed by injecting a material that can gelate in process of time or a non-absorbent material along the absorbent layer cut unit 225.

Although not shown specifically, the absorbent layer 220 is divided into the plurality of the areas with respect to the absorbent layer cut unit 225. The spreading-prevention layer (P) is disposed in a predetermined rim portion of each divided absorbent layer area, in other words, a predetermined rim portion of a divided absorbent area surrounded by the absorbent layer cut unit 225. The separable toilet pad for housebreaking animal companions according to the second embodiment may include a thermal coupling or bonding coupling structure configured to separate the layers from each other, when an external force is applied thereto.

Next, a separable toilet pad for housebreaking animal companions 300 according to a third embodiment of the present invention includes a protection layer 310 having a protection layer cut unit 315, an absorbent layer 320 having an absorbent layer cut unit 325, and the waterproof layer 330. The waterproof layer 330 includes a waterproof layer cut unit 350 formed of a resin composition. The waterproof layer 330 is typically formed of a PE material and the waterproof layer cut unit 350 may be formed of a predetermined material similar to PE, to be manufactured together with the waterproof layer 330. For that, the waterproof layer cut unit 350 may be formed of a mixture of Low-Density Polyethylene (LDPE) and a blowing agent. Alternatively, the waterproof layer cut unit 350 may be formed of High-Density Polyethylene (HDPE).

The separable toilet pad for housebreaking animal companions 300 according to the third embodiment can be cut if necessary and the waterproof function can be performed in waterproof layer cut areas definitely.

Figure 9:
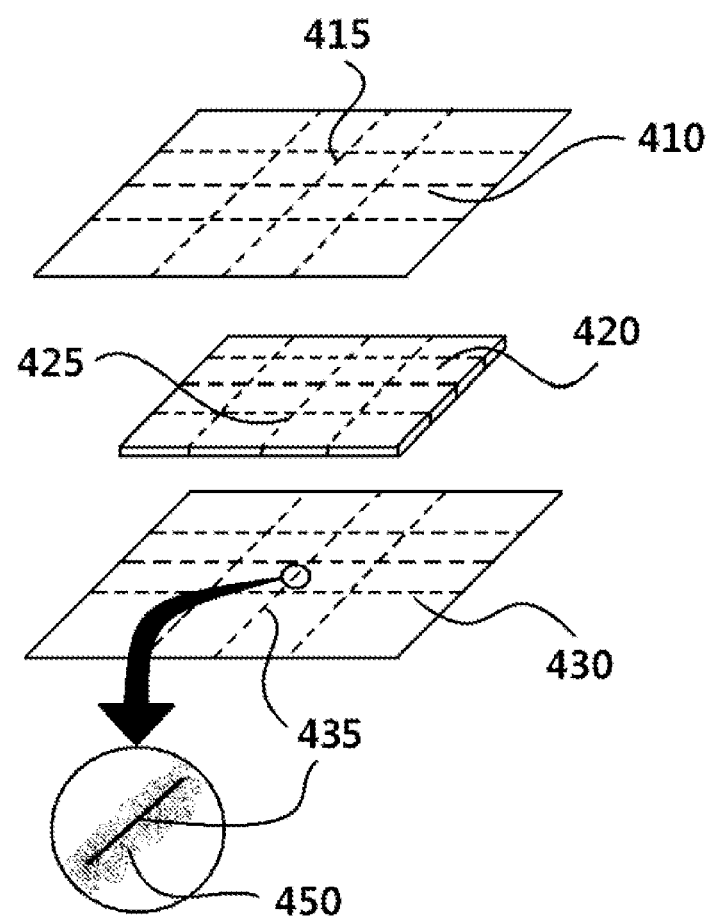
FIG. 9 is an exploded perspective diagram illustrating a separable toilet pad for housebreaking animal companions according to a fourth embodiment of the present invention.

FIG. 9 is an exploded perspective diagram illustrating a separable toilet pad for housebreaking animal companions according to a fourth embodiment of the present invention.

In the separable toilet pad for housebreaking animal companions according to the first embodiment mentioned above, the urine might partially leak to the outside via the waterproof layer cut unit of the waterproof layer, because the absorbent layer that might be too thin or formed of a material having a low absorbent ability fails to absorb the urine completely. If the absorption ability of the absorbent layer is sufficiently high, the separable toilet pad for housebreaking animal companions has no such urine leaking To solve the disadvantage, a separable toilet pad for housebreaking animal companions 400 according to a fourth embodiment of the present invention may further include an auxiliary waterproof member 450 configured to make a waterproof layer cut unit 435 maintain a closed state to prevent the urine from passing there through, when an external force strong enough to tear a waterproof layer cut unit 435 is not applied. The auxiliary waterproof member 450 is especially useful in case the waterproof layer cut unit 435 includes a perforated hole and the filling part is an empty space. At this time, the auxiliary waterproof material 430 may be provided only adjacent to the waterproof layer cut unit 435 or an entire portion of at least one surface of the waterproof layer 430.

When the perforated hole is formed in the waterproof layer cut unit 435, the auxiliary waterproof member 450 can have a predetermined restoring force strong enough to maintain the closed state so as to stop the urine from passing through the perforated hole. The auxiliary waterproof member may be formed of any materials capable of allowing the waterproof layer divided along the waterproof layer cut unit 435 smoothly only when an external force is applied.

If fitted to the purpose of the present invention, a synthetic material, an auxiliary coated material or a gel-like material can be provided in an entire portion of the waterproof layer 430 or near the waterproof layer cut unit 435 as the auxiliary waterproof member. Alternatively, the auxiliary waterproof member 450 may be a vinyl material or pulp material wrapped on an entire portion of the waterproof layer 430. Examples of the vinyl material include plastic wrap or saran or cling wrap. Alternatively, in the separable toilet pad for housebreaking animal companions according to the fourth embodiment, no perforated hole is formed in the auxiliary waterproof member 450 only to enable the waterproof layer tear apart when the external force is applied and simultaneously to prevent the urine from leaking through the waterproof layer cut unit.

Meanwhile, when the waterproof layer cut unit configured of the perforated hole is applied, the waterproof layer may be formed by adding a material having a predetermined restoring force. In other words, the material having the predetermined restoring force is mixed with PE to form the waterproof layer. In this instance, the urine leaking prevention function configured to preventing the urine from leaking through the waterproof layer cut unit can be performed more effectively even without the auxiliary waterproof member.

Next, a method of using the separable toilet pad for housebreaking animal companions according to the embodiments mentioned above will be described. Meanwhile, the using method can be identically applied to the embodiments and the separable toilet pad for housebreaking animal companions 100 according to the first embodiment will be exemplified to explain the using method.

Figure 10:
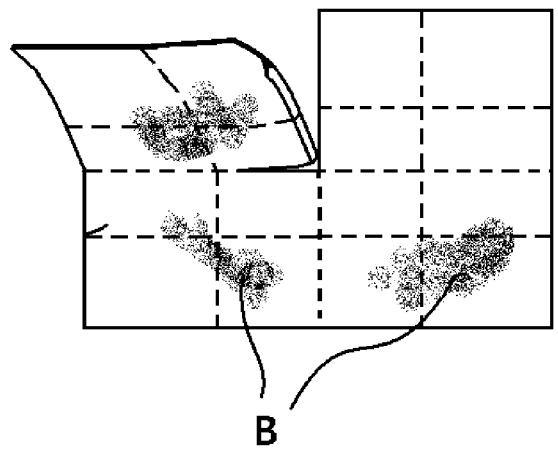
FIG. 10 is a diagram illustrating the separable toilet pad for housebreaking animal companions according to the first embodiment of the present invention that is divided into a plurality of predetermined portions.

FIG. 10 is a diagram illustrating the separable toilet pad for housebreaking animal companions according to the first embodiment of the present invention that is divided into a plurality of predetermined portions. The separable toilet pad for housebreaking animal companions 100 having the structure mentioned above may include the protection layer cut unit 115, the absorbent layer cut unit 125 and the waterproof layer cut unit 135 that are provided in the layers, respectively, such that the user may separate the divided area of the separable toilet pad for housebreaking animal companions with the hand when applying a predetermined external force along the cut units formed in the layers, corresponding to each other easily. In other words, the other clean areas of the separable toilet pad for housebreaking animal companions 100 except the area (B) stained with the dog urine can be separated.

Figure 11:
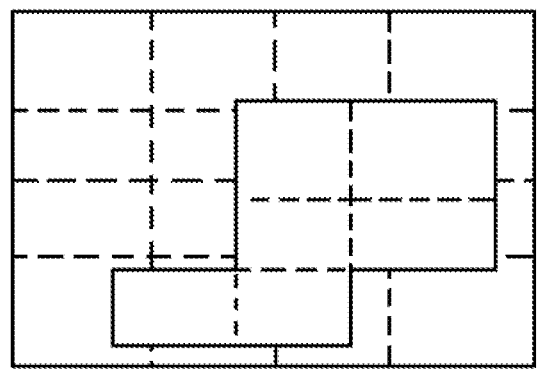
FIG. 11 is a diagram illustrating a state where the separable toilet pad for housebreaking animal companions according to the first embodiment is used.

After that, as shown in FIG. 11, the separated clean separable toilet pad for housebreaking animal companions can be put on a new separable toilet pad for housebreaking animal companions 100 or other separated clean pads can be collected to be used.

Accordingly, the separable toilet pad for housebreaking animal companions according to the embodiments of the present invention has an effective economical advantage that clean areas can be re-used several times. In addition, the area stained with the urine can be removed immediately and the separable toilet pad for housebreaking animal companions according to the embodiments of the present invention has other effective advantages of unpleasant odor removal and visual cleanness.

Various variations and modifications of the femtosecond laser apparatus and the femtosecond laser system including the femtosecond laser apparatus are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

For example, a printed unit having a pigment or paint may be provided along the cut units to make the cut units recognized visually, such that the user can easily recognize and separate the clean areas along the cut units.

Furthermore, a tape or Velcro as a bonding material may be provided in an edge portion of the protection or waterproof layer except the absorbent layer, such that the user can connect the separated clean pad area(s) with other separable toilet pad for housebreaking animal companions easily.

What is claimed is:

1. A separable toilet pad for housebreaking animal companions comprising:
a protection layer covering an exterior surface;
an absorbent layer absorbing and storing urine, the absorbent layer comprising an absorbent material;
a waterproof layer preventing the absorbed urine from leaking; and
a filling part preventing the absorbent material from spreading so that the absorbent material is kept and stored in a predetermined area, wherein,
the protection layer comprises a protection layer cut unit configured to divide the protection layer into two or more independent areas,
the waterproof layer comprises a waterproof layer cut unit corresponding to the protection layer cut unit,
the filling part comprises a filling part cut unit corresponding to the protection layer cut unit, the filling part cut unit being arranged between the protection layer and the waterproof layer, and
the absorbent layer is arranged in the predetermined area of the filling part.

2. The separable toilet pad for housebreaking animal companions according to claim 1, wherein the absorbent layer and the filling part are integrally formed.

3. The separable toilet pad for housebreaking animal companions according to claim 1, wherein the waterproof layer cut unit is formed of a resin composition that has a material different from the material of the waterproof layer.

4. The separable toilet pad for housebreaking animal companions according to claim 1, wherein the waterproof layer cut unit is formed of a mixture of low-density polyethylene and a blowing agent.

5. The separable toilet pad for housebreaking animal companions according to claim 1, wherein the waterproof layer cut unit is formed of high-density polyethylene to form a grained cut line.

6. The separable toilet pad for housebreaking animal companions according to claim 1, wherein,
the waterproof layer cut unit comprises a plurality of perforated holes arranged continuously, and the waterproof layer comprises a material having a predetermined elastic restoring force.

7. A separable toilet pad for housebreaking animal companions comprising:
- a protection layer covering an exterior surface;
- an absorbent layer absorbing and storing urine; and
- a waterproof layer preventing the absorbed urine from leaking, wherein,
- the protection layer comprises a protection layer cut unit configured to divide the protection layer into two or more independent areas,
- the absorbent layer comprises an absorbent layer cut unit corresponding to the protection layer cut unit and a spreading-prevention layer configured to prevent the urine from spreading from a portion of the absorbent layer to another portion with respect to the absorbent layer cut unit,
- the waterproof layer comprises a waterproof layer cut unit corresponding to the protection layer cut unit, and
- each of the protection layer cut unit, the absorbent layer cut unit, and the waterproof layer cut unit is arranged where corresponds to each other, and is cut along each layer cut unit to have two or more independent unit pads.

* * * * *